United States Patent [19]

Ito et al.

[11] Patent Number: 4,892,104
[45] Date of Patent: Jan. 9, 1990

[54] APPARATUS FOR INSPECTING AN ELECTRICALLY STIMULATED HEART

[75] Inventors: Meiichi Ito, Sendai; Kazuya Kuriyagawa, Miyagimachi; Hitoshi Adachi, Tokyo; Kohei Ohno, Higashiyamato, all of Japan

[73] Assignee: Nihon Kohden Corp., Tokyo, Japan

[21] Appl. No.: 251,196

[22] Filed: Sep. 28, 1988

[51] Int. Cl.$^4$ ............................................. A61N 1/00
[52] U.S. Cl. ............................ 128/697; 128/419 PT; 128/710
[58] Field of Search ................. 128/697, 696, 419 PT, 128/702, 710, 712

[56] References Cited

U.S. PATENT DOCUMENTS

| | | | |
|---|---|---|---|
| 3,920,005 | 11/1975 | Gombrich et al. | 128/697 |
| 4,172,459 | 10/1979 | Hepp | 128/697 |
| 4,674,509 | 6/1987 | DeCote | 128/697 |
| 4,791,936 | 12/1988 | Snell et al. | 128/697 |

Primary Examiner—Francis Jaworski
Assistant Examiner—George Manuel
Attorney, Agent, or Firm—Hoffman & Baron

[57] ABSTRACT

Apparatus for inspecting the electrical stimulation of a patients' heart. The apparatus includes a stimulation device in which electrical stimulating wave is generated by an electrical stimulation wave generating device for effecting pacing of a patients' heart in accordance with an externally set stimulation pattern impressed upon the wave and applied to the heart through a catheter, wherein intracardiac electrocardiogram signals are induced, amplified, and recorded on a recorder which is annexed to the stimulation device. The recorder is designed to commence the recording operation in response to a recording start signal in advance of the generation of the final electrical stimulation wave, and to stop the recording operation in response to the intracardiac electrocardiogram signal generated for the first time after the generation of the final electrical stimulation wave. During the operation, waveforms of the final stimulation signal and the intracardiac electrocardiogram signal are recorded and the characters representing the stimulation pattern are printed.

5 Claims, 2 Drawing Sheets

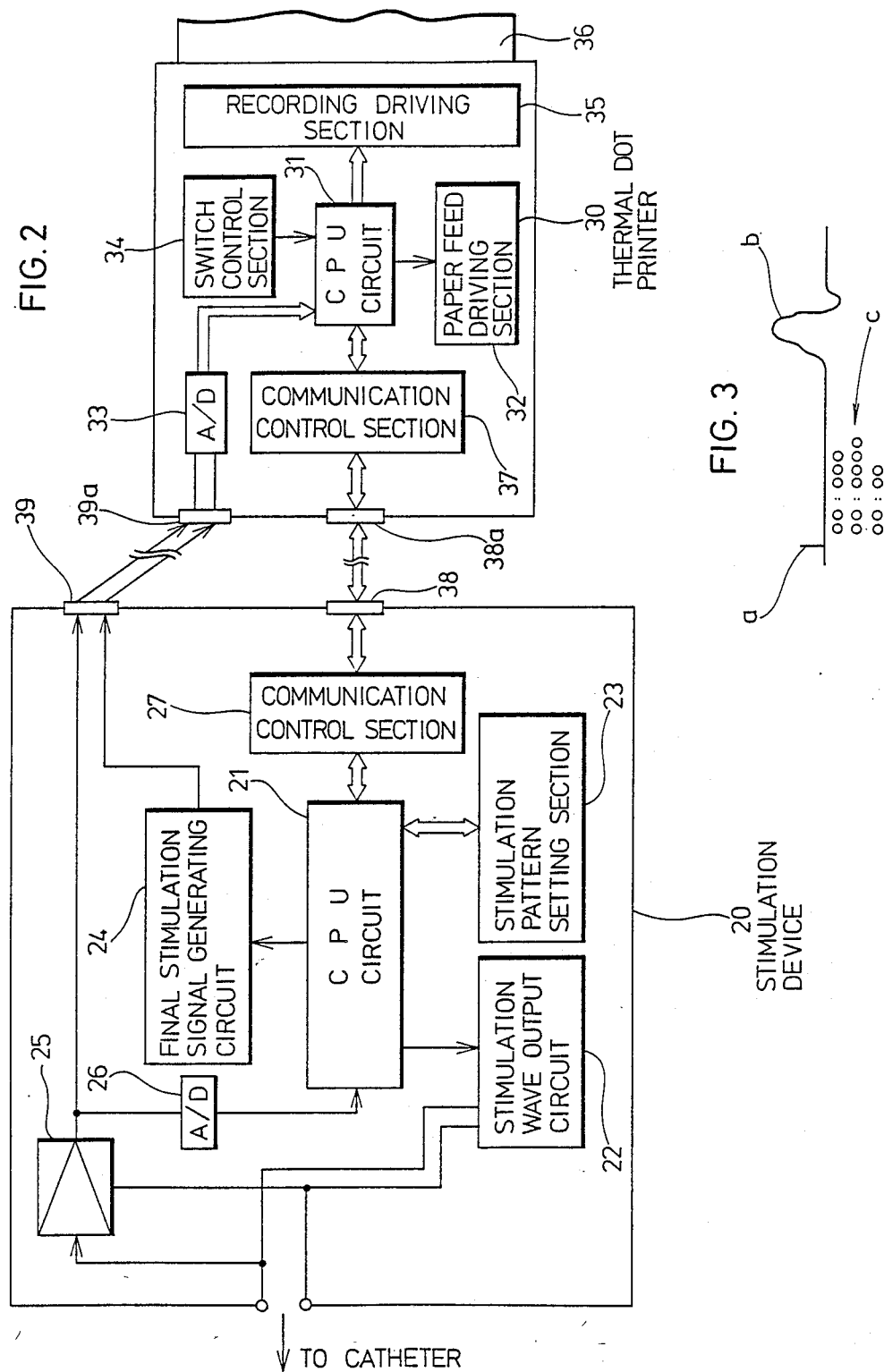

APPARATUS FOR INSPECTING AN ELECTRICALLY STIMULATED HEART

BACKGROUND OF INVENTION

1. Field of the Invention

The present invention relates generally to apparatus for inspecting, i.e. monitoring and recording, the electrical activity of an electrically stimulated heart, and more particularly relates to apparatus of the type including a stimulation device (i.e., a cardiac stimulator), a catheter, and a recorder, wherein the stimulation device generates an electrical stimulative wave which is provided as input through a catheter, to affect heart pacing in accordance with an externally set stimulation pattern, and in the response, intracardiac electro-cardiographic signals are induced in the catheter, amplified and recorded on the recorder which is connected to the stimulation device.

SETTING OF THE INVENTION

Numerous types of biomedical instrumentation are known and available for carrying out various types of electrophysiological study and methodologies In particular, there are several methods of cardiac electrophysiological study which make use of apparatus for monitoring and recording the electrical activity of a heart which has been subject to electrical stimulation as described hereinabove.

In particular, one of these methods is referred to as "the over-drive method", in which a high-frequency stimulating wave is continuously applied to the heart portion of the human body for a predetermined time period, and a measurement is made of the length of time from when the last electrical stimulation is applied until the autochthonous beat occurs. Notably, this time duration is referred to as the so-called sinus function recovery time. In another method known as "early stimulating method", a stimulation wave is applied to the heart such that the interval of the electrical pulse is gradually decreased and the refractory period is measured. Both of these methods make it possible to effectively inspect the function of the sinus knot and stimulation transmission function which can not be determined from ordinary electrocardiograms.

Hitherto, it has been conventional to always keep the recorder operative during the measurement of the sinus function recovery time or the refractory period. Alternatively, however, the user has been required to manually start and stop the recorder in accordance with the timing of the measurement while watching a clock after the start of the stimulation in an effort to save recording paper.

In order to record the stimulation pattern together with the intracardiac electrocardiogram, prior art methods and apparatus have also required writing down by hand directly onto the electrocardiogram, the data concerning the stimulation pattern.

In short, using prior art apparatus for monitoring and recording the response of the heart to electrical stimulation, has been a complicated and laborious procedure.

Accordingly, a primary object of the present invention is to provide apparatus for inspecting the response of the heart to electrical stimulation, where the apparatus is capable of affecting (i) intracardiac pacing by a stimulation device and (ii) recording the intracardiac electrocardiogram on a recorder to thereby enable measurement and recording of the sinus function recovery time.

According to the present invention, the recording of the sinus function recovery time is conducted automatically so as to eliminate the necessity for manual control of the recorder and thereby saves recording paper.

These and other objects of the present invention will be explained hereinafter, and will be more particularly delineated in the appended claims, and other objects of the present invention will hereinafter be apparent to one with ordinary skill in the art to which the present invention pertains.

SUMMARY OF THE INVENTION

According to the present invention, apparatus is provided for automatically inspecting (i.e. monitoring and recording) the electrical activity of the heart, in response to electrical stimulation.

The apparatus includes a stimulation means, a recording start signal generating means, a stimulation pattern generating means, a recording control means, a recording signal generating means, a recording stop generating means, and a catheter.

The stimulation means generates an electrical stimulating wave by an electrical stimulation wave generating means. The electrical stimulating wave effects pacing of the heart in accordance with an externally set stimulation pattern which is applied to the heart through the catheter. Intracardiac electrocardiogram signals are induced in the catheter, which are amplified, and thereafter recorded on a recorder which is connected to the stimulation means.

In the preferred embodiment, the recording start signal generating means is built into the stimulation means and is adapted to generate a recording start signal for starting the recorder in advance of the generating of the final electrical stimulating wave. The stimulation pattern generating means is built into the stimulation means as well, and generates a stimulation pattern signal which is representative of the stimulation pattern. The recording control means is built into the recorder and starts the recording operation in response to the recording start signal, and also stops the recording operation in response to a recording stop signal.

The recording signal generating means generates recording signals in accordance with which, the waveforms of the final stimulation signal and the intracardiac electrocardiogram signal are recorded, and the characters corresponding to the stimulation pattern are printed. The recording stop signal generating means is built into either the stimulation means or the printer (i.e. recorder) and detects the intracardiac electrocardiogram signal generated for the first time after the generation of the final electrical stimulation wave, and generates a recording stop signal after detection of the intracardiac electrocardiogram signal.

As a result of the present invention, various laborious and time consuming efforts controlling the recorder during clinical cardiac electrophysiological inspection. Thus measuring the sinus function recovery time and the refractory time period is made automatic using the apparatus of the present invention.

A principle advantage of the present invention is that in comparison with conventional apparatus, there is a reduction in the man hours required to carry out the measurement of the sinus function recovery time and refractory time period. In addition to relieving the pain of the patient using such apparatus, the consumption of recording paper used with the apparatus of the present invention is substantially minimized.

BRIEF DESCRIPTION OF THE DRAWINGS

FIG. 2 is a block diagram of the preferred embodiment of the apparatus of the present invention; and FIG. 3 is a diagram illustrating an example of a record obtained using the preferred embodiment as shown in FIG. 2.

DESCRIPTION OF THE PREFERRED EMBODIMENTS

Figure 1:
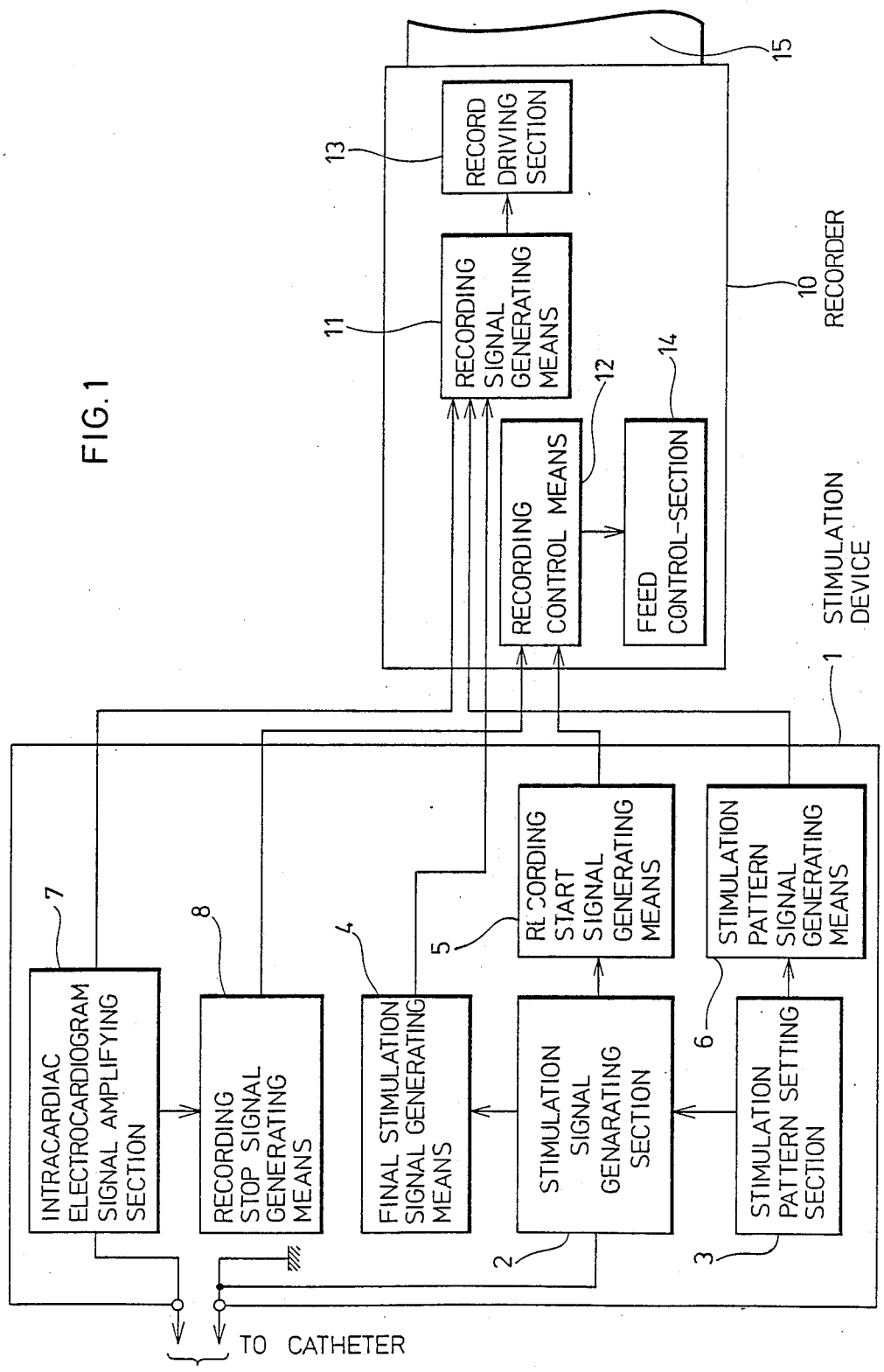
FIG. 1 is a block diagram of an embodiment of the apparatus for inspecting an electrically stimulated heart, constructed in accordance with the principles of the present invention.

Referring to FIG. 1, the apparatus of the present invention is shown comprising a stimulation device 1 and a recorder 10. Stimulation device 1 includes an electrical stimulation wave generating section 2 which generates an electrical stimulation wave in the form of a pulse train, in accordance with a stimulation pattern externally set through a stimulation pattern setting section 3. The electrical stimulation wave generating section 2 applies the the stimulation wave (i.e. electric pulse train) to the heart of the patient through a catheter, in an electrically-isolated manner.

The stimulation device 1 also includes an intracardiac electrocardiogram signal amplifying section 7 which amplifies in an electrically-isolated manner, the intracardiac electrocardiogram signal induced in the catheter. Stimulation device 1 further includes the following components; final stimulation signal generating means 4 which generates a signal at a timing corresponding to the final pulse of the electrical stimulation signal; recording start signal generating means 5 for generating a signal for starting a recorder 10 in advance of the generation of the final stimulation signal; stimulation pattern signal generating means 6 for generating a stimulation pattern signal representative of the stimulation pattern; and recording stop signal generating means 8 for generating a recorder stop signal upon detection of the first autochthonous beat.

The recorder 10 annexed to the stimulation device 1, has a control unit 14 and a record driving unit 13. The control unit 14 for controlling the feed of recording paper 15 and a record driving unit 13 is for recording characters and signal waveforms on the recording paper 15 in response to recording signals input thereto. The recorder 10 also incorporates a recording signal generating means 11, and a recording control means 12. The recording signal generating means 11 is for recording the input final stimulation signal and intracardiac electrocardiogram waveforms, while causing the recorder to print data correspond to electrical stimulation data. On the other hand, the recording control means 12 is for starting the recording operation in response to a recording start signal, and for stopping the recording operation in response to the recording stopping signal.

In the measurement of the sinus function recovery time or the refractory period, the electrically isolated (i.e. "floating") stimulation signal generating section 2 of the stimulation device 1, applies electrical stimulation to the heart throughout the catheter in accordance with the stimulation pattern which has been externally set by the stimulation pattern setting section 3. The recording start signal for generating means 5 delivers a recording start signal in response to a timing signal which is generated in advance of the delivery of the final electrical stimulation pulse. The final stimulation signal generating means 4 then delivers a final stimulation signal in synchronization with a timing signal which is generated when the final stimulation pulse is generated Thereafter, the stimulation pattern signal generating means 6 delivers a stimulation pattern signal corresponding to the externally set stimulation pattern, in response to the delivery of the recording start signal.

After the determination of the sinus function recovery time or the refractory period, and autochthonous intracardiac electrocardiogram signal is induced in the catheter and is delivered through the intracardiac electrocardiogram signal amplifying section 7. Upon detection of the thus delivered intracardiac electrocardiogram signal, the recording stop signal generating means 8 delivers the recording stop signal when a predetermined period has lapsed after detection of the intracardiac electrocardiogram signal. Meanwhile, the recording control means 12 in the recorder 10 operates in response to the recording start signal so as to activate at least the feed control section 14 to thereby commence the feeding of the recording paper 15.

In response to the final stimulation signal, the recording signal generating means 11 operates so as to enable the record driving section 13 to scribe on the recording paper 15 the waveform of the final stimulation signal. The recorder 10 continues to operate from the moment of generation of the final stimulation signal, until the sinus function recovery time expires. When the first autochthonous beat is detected, the recording signal generating means 11 operates to scribe the waveform of the beat and then the recording control means 12 operates in response to the recording stop signal and thereby terminates at least the paper feed operation. Meanwhile, the recording signal generating means 11 operates to enable the recorder to record the stimulation pattern in response to the stimulation pattern signal.

The described embodiment above can be modified such that the final stimulation signal generating means 4 is constructed part of recorder 10 so as to generate the final stimulation signal after determination of a predetermined period after the generation of the recording starting signal. The recording stop signal generating means 8 may also be realized that part of the recorder 10 so as to generate the recording stop signal in response to an intracardiac electrocardiogram signal.

Referring now to FIG. 2, the preferred embodiment of the apparatus of the present invention is shown. In this embodiment, a thermal dot printer 30 functions as the recorder 10 of FIG. 1, and is connected to the stimulation device 20 through connectors 38, 38a, and connectors 39 and 39a.

The stimulation device 20 includes a central processing unit (hereinafter CPU) circuit 21 having various circuits such as a ROM, a RAM, a clock generator and so forth which together constitute the recording start signal generating means 5, stimulation pattern signal generating means 6 and the recording stop generating means 8 which are described in the embodiment shown in FIG. 1.

The CPU circuit cooperates with a stimulation wave output circuit 22, forming part of the electrical stimulation wave generating section 2. A reference numeral 23 denotes a keyboard-type stimulation pattern setting section through which the characteristics of the stimulation pattern are set. Notably, the stimulation pattern characteristics include the type of stimulation, the stimulation interval, the stimulation time, and so forth. The stimulation setting pattern section also delivers a code signal which represents the set key position.

Reference numeral 24 designates a final stimulation signal generating circuit comprising a pulse generating circuit adapted to be triggered by a timing signal from the CPU circuit 21, and which generates the final stimulation signal a. The stimulation device 20 further includes an amplifier 25, an A/D converter 26, and a communication control section 27.

The amplifier 25 is for amplifying the intracardiac electrocardiogram signal induced in the catheter, whereas the A/D converter 26 is for converting the output of the amplifier 25 into digital signals. The communication control section 27 on the other hand, is a device which meets the serial transmission standard of RS-232-C and is capable of conducting transmission of the digital signals (e.g. a recording start command signal, recording stop command signal and a stimulation pattern command signal) through a signal exchange between itself and the communication control section 37 of the thermal dot printer 30. The output portion of the stimulation wave output circuit 22 and the input portion of the amplifier 25 are electrically isolated (i.e. "electrically floating") through an isolating coupling circuit such as a transformer.

The CPU circuit 21 is adapted for supplying the stimulation wave output circuit 22 with the stimulation wave signal of the pattern which has been set through the stimulation pattern section 23. This enables the stimulation wave output circuit 22 to deliver to the catheter, the stimulation wave which has been formed as a pulse train and which has been amplified. Thereafter, a recording start command signal of a predetermined format, is delivered through the communication control section 27 at a predetermined moment which is for example, three seconds in advance of the generation of the final stimulation wave. Immediately after delivery of the recording start signal, the CPU 21 delivers a stimulation pattern command signal of a predetermined format having factors such as the type of stimulation pattern, stimulation interval, stimulation time and so forth. At the moment of generation of the final stimulation wave, the CPU circuit 21 delivers a trigger signal to the final stimulation signal generating circuit 24 thereby enabling the latter to produce the final stimulation signal a.

Subsequently, the CPU circuit 21 operates to (i) pick up the intracardiac electrocardiogram signal which is generated for the first time after the generation of the final stimulation wave, and (ii) detect the change in the amplitude of the intracardiac electrocardiogram signal b. The CPU circuit 21 then delivers a recording stop signal of a predetermined format to the communication control section 27, when a predetermined time, e.g., five seconds, has lapsed after the rise of the intracardiac electrocardiogram signal b.

The thermal dot printer 30 also includes a CPU circuit 31 which is adapted to receive signals such as a power on/off signal, and a recording speed signals through a switch control section 34. CPU circuit 31 is also adapted to receive various hereinbefore mentioned command signals through the communication control section 37. Thus, the CPU circuit 31 comprises the recording signal generating means 11 and the recording control means 12, both of which have been described hereinbefore in connection with the apparatus of FIG. 1.

The printer 30 also includes a paper feed driving section 32, and a recording driving section 35. The paper feed driving section 32 starts and stops the feed of the recording paper in accordance with a signal received from the CPU circuit 31, whereas the recording driving section 35 drives thermal head upon the receipt of the dot recording signal from the CPU circuit 31.

The CPU circuit 31 receives a recording start command signal and a recording stop command signal from the communication control section 37, and delivers paper feed start and stop signals through the paper feed driving section 32, in order to start and stop feeding of the recording paper 36 upon reading these command signals.

The CPU circuit 31 is also operable for the purpose of converting the final stimulation signal and the intracardiac electrocardiogram signal b into dot recording signals corresponding to the waveforms of the respective signals. Notably, this A/D conversion process is carried out by passing the signals through the A/D converter 33.

CPU circuit 31 also reads the stimulation pattern command signal, and reads from a memory, the dot recording signals corresponding to one-line character data corresponding to the stimulation pattern. The dot recording signal thus read, is supplied through the recording driving section 35.

The manner in which the above-described apparatus operates is described hereinbelow.

This stimulating heart inspection apparatus operates in a manner which will be explained hereinunder. A desired stimulation pattern is selected through the stimulation pattern setting section 23 in the stimulation device 20. Then, the CPU circuit 21 forms a stimulation wave signal to the stimulation wave output circuit 22 to enable the circuit 22 to apply an electrical stimulation wave to, for example, atrium of heart through the catheter. Meanwhile, the power supply to the thermal dot printer 30 has been turned on by the operation of the switch control section 34, and the recording speed signal also has been set beforehand. Then, the recording start command signal is supplied to the CPU circuit 31 of the thermal dot printer 30 through the communication control section 27 at a moment which is three (3) seconds ahead of the final stimulation wave.

Upon reading the recording start command signal, the CPU circuit 31 operates by starting the feeding of the recording paper. After elapse of about three (3) seconds through the A/D converter 33, the final stimulation signal a is supplied, and changed into a digital signal. The digital signal is then changed by the CPU circuit 31 into dot recording signals in accordance with which dot printing elements of the recording head are driven by the recording driving section 35, whereby the waveform is recorded as illustrated in FIG. 3.

For instance, the first autochthonous intracardiac electrocardiogram signal b is received after elapse of 2 seconds from the start of the recording, and the thus received signal b is converted by the CPU circuit 31 into dot wave signal, whereby the waveform of this signal is written on the recording paper 36. Upon detection of the intracardiac electrocardiogram signal b, the CPU circuit 21 generates a recording stop command signal at a moment which is about five (5) seconds after the detection of the signal b. In response to this stop command signal, the CPU circuit 31 of the printer 30 operates to stop the feed of the recording paper 36. Before stopping the feed of the recording paper 36, the CPU circuit 31 operates to convert the stimulation command signal into dot recording signals so as to enable the stimulation pattern data c to be printed.

Although the invention has been described through specific forms, it is to be understood that the described embodiments are only illustrative and various changes and modifications may be imparted thereto without departing from the scope of the invention.

For instance, the final stimulation signal generating circuit 24 may be designed to produce a plurality of consecutive pulses rather than a single pulse. It is also possible to arrange the components of the present invention such that the recording start signal generating means 5 controls not only the paper feed, but also other types of control such as the control of the recording control means 12 by a command signal which appoints the recording pattern corresponding to the stimulation pattern.

While the particular embodiments shown and described above have proven to be useful in many applications involving the above-mentioned art, further modifications herein disclosed will occur to persons skilled in the art to which the present invention pertains and also such modifications are deemed to be within the scope and spirit of the present invention defined by the appended claims.

What is claimed is:

1. Apparatus for inspecting the electrical stimulation of a patient's heart, said apparatus including a stimulation means wherein an electrical stimulating wave is generated by an electrical stimulation wave generating means so to effect pacing of said heart in accordance with an externally set stimulating pattern impressed upon said wave and applied to said heart through a catheter, wherein intracardiac recorded on a recorder which is annexed to said stimulation means, said apparatus comprising:
    (a) a final stimulation signal generating means for generating a final stimulation signal at a timing corresponding to a final electrical stimulation wave;
    (b) a stimulation pattern generating means for generating a stimulation pattern representative of said stimulation pattern;
    (c) a recording start signal generating means for generating a recording start signal for starting said recorder in advance of said generation of said final electrical stimulating wave;
    (d) detecting said intracardiac electrocardiogram signal generated for the first time after said generation of said final electrical stimulation wave, and for generating a recording stop signal after the detection of said intracardiac electrocardiogram signal;
    (e) a recording signal generating means for generating recording signals in accordance with which, the waveforms of said final stimulation signal and said intracardiac electrocardiogram signal are recorded, and the characters corresponding to said stimulation pattern are printed by said recorder; and
    (f) a recording control means for starting the recording operation of said recorder in response to said recording start signal and stopping the recording operation in response to a said recording stop signal.

2. The apparatus of claim 1 wherein said recording start signal generating means, said stimulation pattern signal generating means are disposed in said stimulation means, and, wherein said recording control means is disposed in said recorder and both said recording stop signal generating means and said final stimulation signal generating means are disposed in one of said stimulation means and said recorder.

3. The apparatus of claim 1, wherein said recording start signal generating means, said stimulation pattern signal generating means, said recording stop signal generating means, and said electrical stimulation wave generating means comprises a central processing unit circuit incorporated into said stimulation means.

4. The apparatus of claim 1, wherein said recording signal generating means and said recording control means comprise a central processing unit circuit incorporated into said recorder.

5. Apparatus of claim 1, wherein said recording start signal generating means is capable of generating said recording start signal at a moment which is several seconds before the generation of said final electrical stimulation wave, and wherein said recording stop signal generating means is capable of generating said recording stop signal at a moment which is several seconds after the rise of the amplitude of the first intracardiac electrocardiogram signal.

* * * * *